United States Patent [19]
Jacobsen et al.

[11] Patent Number: 5,941,914
[45] Date of Patent: Aug. 24, 1999

[54] ARTICULATED, STACKED-PLATE ARTIFICIAL BODY PART

[75] Inventors: Stephen C. Jacobsen; Joseph Anthony Jacobs; Fraser M. Smith, all of Salt Lake City, Utah

[73] Assignee: Sarcos L.C., Salt Lake City, Utah

[21] Appl. No.: 08/956,207

[22] Filed: Oct. 22, 1997

[51] Int. Cl.⁶ ................................................ A61F 2/54
[52] U.S. Cl. ............................ 623/64; 414/1; 901/28
[58] Field of Search ........................ 623/63–65; 446/375, 446/376, 390; 901/28; 414/1, 744.5

[56] References Cited

U.S. PATENT DOCUMENTS

| | | | |
|---|---|---|---|
| 559,593 | 10/1896 | Voegtlein | 623/64 |
| 1,507,682 | 9/1924 | Pecorella et al. | 623/64 |
| 2,285,885 | 6/1942 | Becker | 623/64 |
| 2,464,577 | 3/1949 | Hobbs | 623/63 |
| 2,493,776 | 1/1950 | Pecorella et al. | 623/64 |
| 3,345,647 | 10/1967 | Gentiluomo | 623/63 |
| 3,694,021 | 9/1972 | Mullen | 623/64 |
| 4,094,016 | 6/1978 | Eroyan | 623/63 |
| 4,364,593 | 12/1982 | Maeda | 623/64 |
| 4,673,790 | 6/1987 | Sawada et al. | 219/69 W |

*Primary Examiner*—Mickey Yu
*Assistant Examiner*—Bruce E. Snow
*Attorney, Agent, or Firm*—Thorpe North & Western LLP

[57] ABSTRACT

An artificial finger assembly including articulating finger segments constructed of stacked and aligned plates. The finger segments are coupled to adjacent finger segment at common pivot points along a top edge of the assembly. The finger segments are caused to pivot around the common pivot points by a lever arm comprised of a series of articulated lever arm plates. The lever arm plates are coupled to the finger segments along an axis offset to one side of the common pivot points and parallel to the finger segments.

32 Claims, 4 Drawing Sheets

ARTICULATED, STACKED-PLATE ARTIFICIAL BODY PART

BACKGROUND OF THE INVENTION

1. Field of the Invention

This invention pertains to artificial body parts which can simulate movement of the body part they replace. More particularly, an artificial finger is envisioned which can simulate movement of a human finger. A plurality of articulated segments are linked together to form a coordinated assembly actuated by a single motivating means, thereby enabling the device to provide human hand-like motion and action.

2. State of the Art

Technology is advancing to the point where creating artificial body parts or limbs goes beyond simply imitating the function of the lost limb. Helping a person to cope with loss of a limb can now be furthered by replacing the limb with one that can also take on the appearance of the original limb.

For example, providing a prosthesis for a person who has lost a hand or arm enables the person to have a substantial portion of the function of the missing limb returned. However, an even greater benefit is obtained when the prosthesis resembles the missing limb, and duplicates the motion and as well as the function.

This invention relates specifically to replacement of an intricate body part, a finger. The intricacy of the motion of the finger is a significant reason why replacing the function often falls short of also duplicating the appearance at the same time. We are forced to wait until techniques of manufacturing and materials used in construction advance to the point where experimentation becomes possible.

While prosthetics is the most obvious advantage of an artificial finger, another advantage comes from providing the function of an artificial finger to robotic devices. In our attempt to humanize technology to make it less intimidating to the average person, it has been proposed that we might succeed by shrouding artificial devices in a cloak of human appearance. A hand created using an assembly of fingers that not only appear human but duplicate the range of motion of human fingers would satisfy this need.

Prior art attempts to create artificial fingers have produced assemblies which suffer from various drawbacks. For example, overall bulk of the finger assembly is typically greater than a human hand. With the added bulk comes weight which requires that the servomotors driving the fingers be powerful, and thus larger and consequently more demanding of energy, and ultimately impractical.

The prior art artificial fingers are also complicated in terms of the number and complexity of parts, reflecting the nature of the part being replaced. For example, devices which rely on pulley systems to control movement have cables that can wear out, fray and break, fall off of pulley wheels, etc.

Accordingly, the challenge in designing an artificial finger assembly, which could replace a substantial portion of the form and function of actual human fingers, comes from designing an assembly that is mechanically simple to build and easy to manipulate without the complexity of prior designs. The fingers should be implemented such that a curling/gripping motion is initiated by actuation of a single lever arm at the base of the finger. Such a design should reduce the size of the fingers as well as the lever arm means for actuating the finger. The design would also be easy to operate.

OBJECTS AND SUMMARY OF THE INVENTION

It is an object of the present invention to provide an artificial finger generally capable of providing the movement of a human finger.

It is another object of this invention to provide an artificial finger which duplicates the shape of a human finger.

It is yet another object of the present invention to provide an artificial finger which can grip objects by applying pressure from a plurality of different sides so as to partially or completely encircle objects as would a human finger.

It is a further object of the invention to provide a method of manufacturing an artificial finger such that the separate finger components are easily cut and assembled.

It is yet a further object of the present invention to provide an artificial finger which is inexpensive and economical to manufacture.

Still yet another object of the invention is to provide an artificial finger having a plurality of coordinated linkage segments such that all segments are connected in series, and movement of a single lever arm causes movement in each segment relative to other segments along an edge of pivot points.

It is another object of the present invention to provide an artificial finger having at least one range of motion restrictor so that a maximum range of motion of the linkage segments can be selected.

These and other objects are realized in an artificial finger assembly comprised of articulating finger segments constructed of stacked and aligned plates. A plurality of the finger segments are coupled to adjacent finger segments at common pivot points along a top edge of the assembly. The finger segments are caused to pivot around the common pivot points by a lever arm comprised of a series of articulated lever arm plates. The lever arm plates are coupled to the finger segments along an axis offset to one side of the common pivot points and generally parallel to the finger segments.

In another aspect, a plurality of range of motion restrictors are coupled to a back side or edge of the finger linkage segments, thereby preventing movement of the finger segments beyond a pre-selected range of motion.

These and other objects, features, advantages and alternative aspects of the present invention will become apparent to those skilled in the art from a consideration of the following detailed description taken in combination with the accompanying drawings.

DETAILED DESCRIPTION OF THE INVENTION

Reference will now be made to the drawings in which the various elements of the present invention will be given numerical designations and in which the invention will be discussed so as to enable one skilled in the art to make and use the invention. It is to be understood that the following description is only exemplary of the principles of the present invention, and should not be viewed as narrowing the claims which follow.

The presently preferred embodiment is directed toward applying the principles of the present invention in the creation of an artificial, segmented (jointed) finger assembly. However, it should be understood that the principles of the present invention can be applied to the creation of any artificial limb, such as an arm, a leg, a foot, etc. Accordingly, the artificial limb can be referred to as an artifical body segment assembly.

Figure 1:
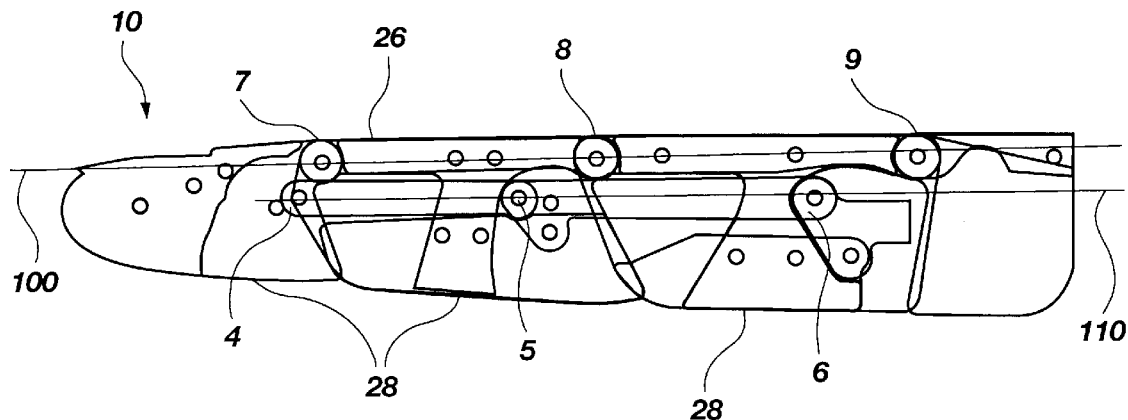
FIG. 1 is an elevational profile view of an artificial finger made in accordance with the present invention.

FIG. 1 is a phantom plan profile view of the artificial finger assembly 10 made in accordance with the preferred embodiment of the present invention. The profile gives an indication of the appearance of the outline of the assembly 10. As shown, the assembly 10 is cut so as to have the profile of a human finger which adds to the realism of the finger as a prosthesis. The phantom aspect of the illustrated assembly 10 also reveals the hidden structure within the assembly 10 which enables the finger to bend as it does.

The view essentially illustrates all of the important detail of the plates because each plate seen edgewise is a flat plate of metal with no protruding contours or features that might indicate function. Each plate will be illustrated in a profile view in FIGS. 3A–3E to clearly show the interrelationship between them.

Figure 2:
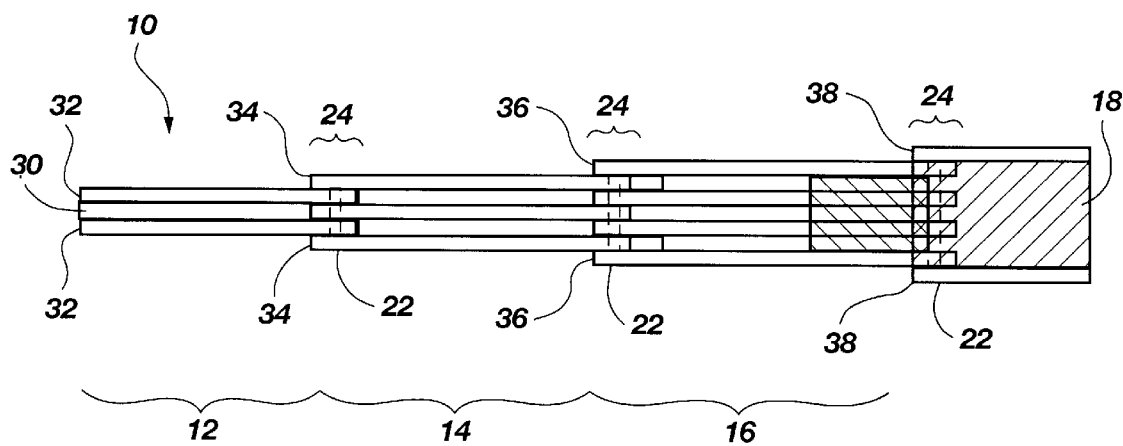
FIG. 2 is a top plan view of the artificial finger of FIG. 1.

FIG. 2 is a plan view of the artificial finger assembly of FIG. 1. Because of the viewing angle, the relationship of the plates is now revealed to comprise a plurality of interlocking plates beginning at a fingertip and expanding to become increasingly wider as each successive segment adds an additional layer of outer plates. In this embodiment, the assembly 10 is comprised of a center segment 30, a pair of first outer segments 32 each being as long as the center segment 30, a pair of second outer segments 34 being shorter than the pair of first outer segments 32, a pair of third outer segments 36 being shorter than the pair of second outer segments 34 and a pair of fourth outer segments 38 being shorter than the pair of third outer segments 36. The pair of fourth outer segments 38 connect to a base 18.

There are a total of three pivoting segments, 12, 14 and 16 in the articulated finger assembly 10 shown. The rearward segment forms the base 18, such as a palm of a hand. The pivoting segments 12, 14 and 16 move relative to this base 18 to grip an object by partially encircling it so as to push the object against the base 18 or against the other pivoting segments 12, 14 and 16. The first pivoting segment 12 is comprised of the center segment 30 and the pair of first outer segments 32. The second pivoting segment 14 is comprised of the elements of the first pivoting segment 12 and the pair of second outer segments 34. The third pivoting segment 16 is comprised of the elements of the second pivoting segment 14 and the pair of third outer segments 36.

As also indicated in FIG. 2, the plates of the articulated finger assembly 10 partially overlap. The plates are coupled by a pin (not shown) inserted into a hole illustrated as a dotted line 22 through the innermost plates, but not through the outermost plates. The outermost plates at each segment juncture 24 are cover plates which hold the pins (not shown) in place. By coupling a pin to each of the outermost plates at each juncture 24, the outermost plates are held in place in relation to each other as the articulated pivoting segments 12, 14 and 16 pivot at the segment junctures 24.

The articulated finger assembly plate segments are joined. These segments are joined only along the top edges 26 seen in FIG. 2. By causing the assembly 10 to pivot along these top edges 26, the bottom edges 28 of the plates are free to slide past each other as the assembly 10 is caused to move.

It should be noted that while the articulated finger assembly 10 shown is comprised of a specific number of articulating segments, the present invention could be modified to have more or less articulated segments. Therefore, the scope of this invention includes articulated finger assemblies having a plurality of pivot points, or joints. For example, removing one articulated segment results in a finger having the same number of pivot points as a thumb. Increasing the number of articulated segments results in an artificial finger having smoother curves as it bends.

FIGS. 3A–3E illustrate the individual plates which make up each of the pairs of first, second, third and fourth outer segments 32, 34, 36 and 38, and the single center assembly 30. Each of the individual plates will be discussed in relation to other plates to which it is coupled.

Figure 3A:
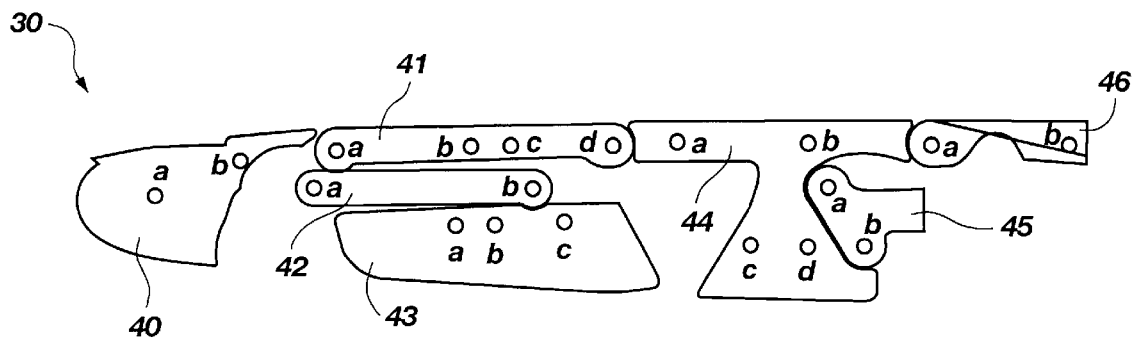
FIGS. 3A–3E is a series of elevational profile views illustrating the various layers of plates that comprise the artificial finger and the lever arm of the present invention.
Figure 3B:
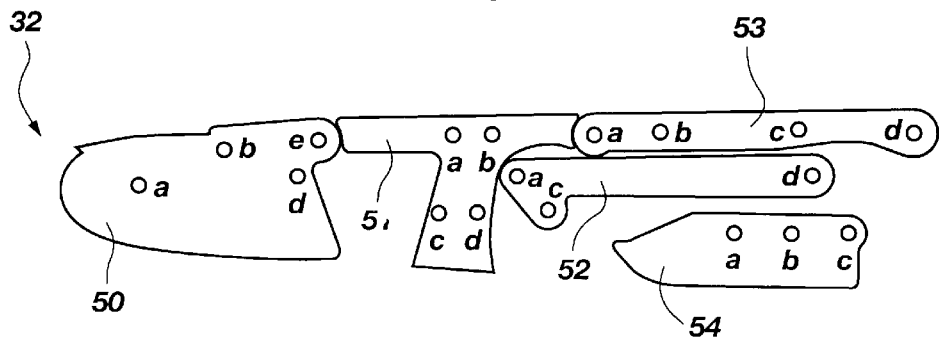
Figure 3C:
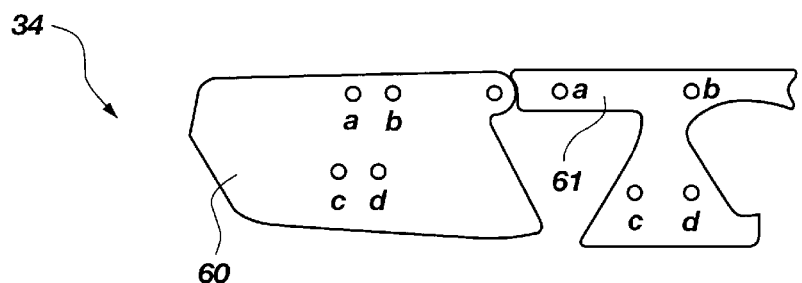
Figure 3D:
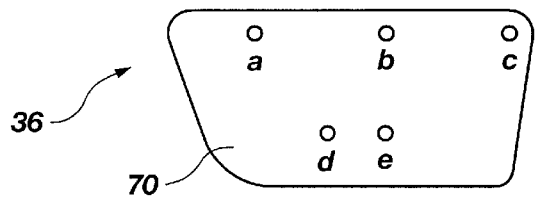
Figure 3E:
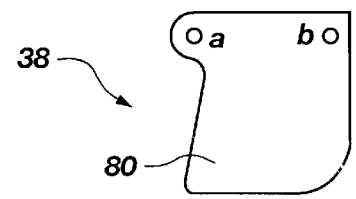
Figure 4A:
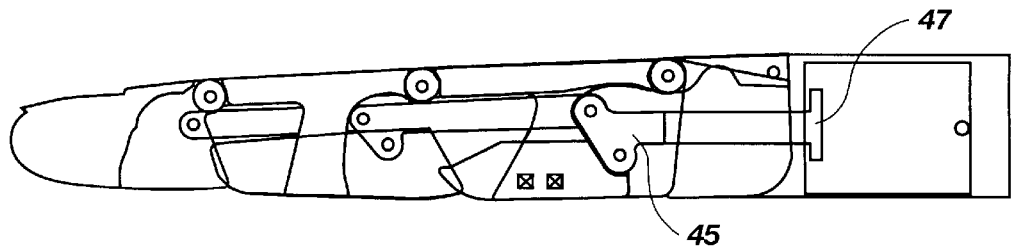
FIGS. 4A–4D is a series of elevational profile views illustrating movement of the artificial finger plates upon actuation of the lever arm.
Figure 4B:
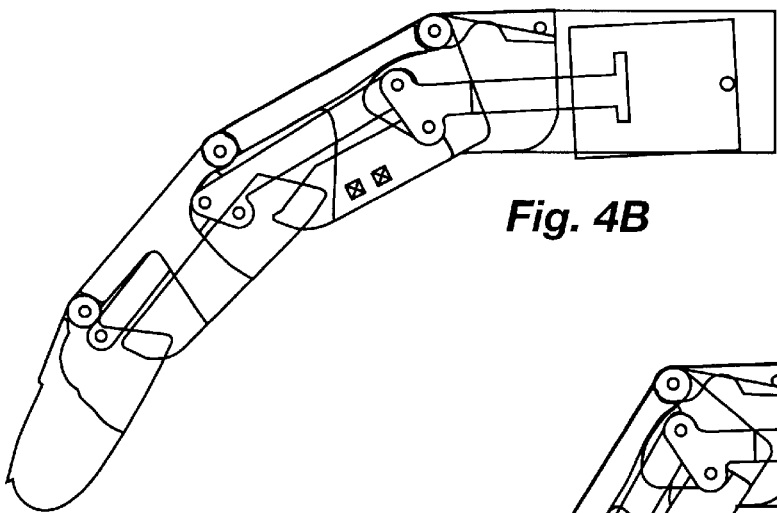
Figure 4C:
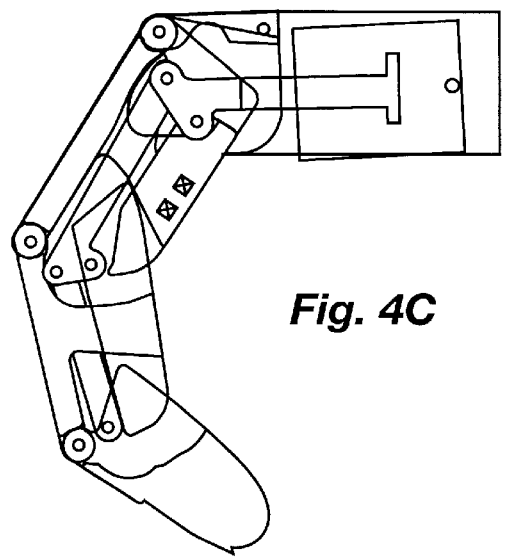
Figure 4D:
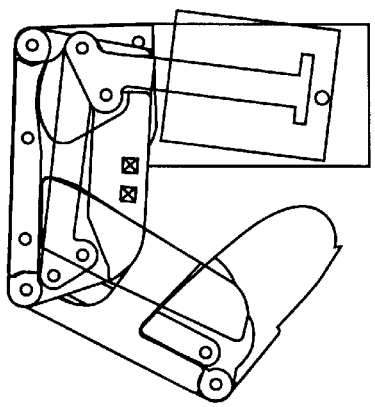

FIG. 3A illustrates the seven individual plates 40, 41, 42, 43, 44, 45 and 46 which comprise the center assembly 30 of the artificial finger assembly 10. Some of the unique features of the plates are the shape and selective placement of holes through the plates. Hole placement is determined based on the function of the plate. For example, plate 40 has two holes 40a and 40b. The function of both holes 40a and 40b is to secure plate 40 to plate 50 of the pair of first outer segments 32. However, while holes 41b and 41c of plate 41 also act to secure plate 41 to plate 51 of the pair of first outer segments 32, holes 41a and 41d are pivot holes. Pins inserted through holes 41a and 41d allow plate 41 to pivot with respect to plates 50 and 53 by also passing the pin through holes 50e and 53a respectively. Therefore, holes either secure a plate to other plates, or enabling a plate to pivot with respect to other plates.

Plate 42 is a lever arm plate. Lever arm plates form the assembly of plates which cause the articulated finger assembly 10 to move. Plate 42 has two pivot holes, 42a and 42b, which enable a pin to be coupled to the pair of plates 50 through holes 50d, and couple to pair of plates 52 through holes 52a.

Plate 43 has two securing holes 43a and 43b which secure the plate 43 to the pair of plates 51 by a pin through holes 51c and 51d. Pivot hole 43c couples to pair of plates 52 by a pin through holes 52c.

Plate 44 has four securing holes 44a, 44b, 44c and 44d to secure plate 44 to pairs of plates 52, 53 and 54. Pivot hole 44a couples to pair of plates 53 by a pin through hole 53b. Pivot hole 44b couples to pair of plates 53 by a pin through hole 53c. Pivot hole 44c couples to pair of plates 54 by a pin through hole 54a. Pivot hole 44d couples to pair of plates 54 by a pin through hole 54b.

Plate 45 is a lever arm, whereby the articulated finger assembly 10 is caused to bend by retracting the lever arm 45. Plate 45 has two pivot holes. Pivot hole 45a couples to pair of plates 52 by a pin through hole 52d. Pivot hole 45b couples to pair of plates 54 by a pin through 54c.

Finally, plate 46 has two holes, 46a and 46b. Pivot hole 46b couples to pair of plates 53 by a pin through 53d. Securing hole 46b couples to pair of plates 38 by a pin through 80b.

The above description gives all interconnections between the center assembly 30 plates and the pair of first outer segments 32. The following description gives all interconnections between the pair of second outer segments 34 and the pair of first outer segments 32, and the pair of second outer segments 34 and the pair of fourth outer segments 36.

Plate 60 of the pair of second outer segments 34 has four securing holes, 60a, 60b, 60c and 60d, and one pivot hole 60e. Securing holes 60a, 60b, 60c and 60d couple to pair of plates 51 by a pin through each corresponding securing hole 51a, 51b, 51c and 51d. Pivot hole 60e couples to pair of plates 53 by a pin through 53a. Another feature of plate 60 is that the plate serves to cover holes, and thereby prevent a pin inserted in the holes from falling out. Specifically, plate 60 covers holes 50d, 50e, 52a and 52c.

Plate 61 has four securing holes, 61a, 61b, 61c and 61d. Pins 61a and 61b couple to plate 53 and corresponding holes 53b and 53c respectively by pins inserted therethrough. Pins 61c and 61d couple to plate 54 and corresponding holes 54a and 54b by pins inserted therethrough.

Plate 61 also couples to plate 70. Securing holes 61a, 61b, 61c and 61d couple to corresponding holes 70a, 70b, 70d and 70e respectively by pins inserted therethrough.

Plate 70 couples to plate 80 by a pivot hole. Pivot hole 70c couples to pivot hole 80a by a pin inserted therethrough.

The above specification discloses all interconnections of the plates of segments 30, 32, 34, 36 and 38 by describing the function of the holes formed therein. However, it is also the shape of the plates which enables the invention to function as claimed. Therefore, the next portion of this disclosure explains how the interactions of the interconnected plate segments results in coordinated movement so as to provide motion of a human finger.

What might not yet be understood from the description of the pivot hole and the securing hole connections between plates is that the pivots holes form two separate linkage axes 100 and 110 as shown in FIG. 1. The first linkage axis 100 is formed of the primary pivot joints 7, 8 and 9, and plates 40, 41 44 and 46 of the articulated finger assembly 10. The second linkage axis 110 is formed of the lever arm pivot joints 4, 5 and 6, and plates 42, 45, 50 and 52. Crucial to the operation of the articulated finger assembly 10 is the placement of these axes 110 and 110. The first linkage axis 100 is along the top edges 26 of the assembly 10. The second linkage axis 110 is close to and generally parallel with the first linkage axis 100. This means that there are no pivot points along the bottom edges 28 of the assembly.

It should also be apparent that it is important that the lever arm plates be coupled to the finger segments on an offset axis. If the axis were not offset, applying a force to the linkages would not result in movement. However, in the presently preferred embodiment, offsetting the axis will cause all of the linkages to move toward the axis. In other words, the linkages will all move so as to curl inward, just like a finger being bent.

Another important consideration is that it is not required that the linkage axes be parallel. What is important is that the linkage plates be constructed in such a way that they can move relative to each other, even if not in parallel. This should not be construed to mean that the range of motion of the linkage plates is even reduced. Therefore, while the presently preferred embodiment is directed to parallel linkages because it is most appropriate for this application, it should not be considered a fundamental restraint.

Linkage axis 100 and 110 placement is crucial to the operation because it enables symmetrical and coordinated movement of each segment as the lever arm is actuated. As demonstrated by the sequence of FIGS. 4A, 4B, 4C and 4D, plate 45 is coupled to an extension member so as to facilitate a pulling action on plate 45. As plate 45 is pulled, it in turn pulls on coupled plate 52, which in turn pulls on plate 42, which pulls on plate 50.

Pulling on the plates that form the lever arm would have no impact on surrounding non-lever arm plates if they were not also coupled to non-lever arm plates. For example, plate 45 is also coupled to plates 54, which in turn are coupled to plates 44, 61 and 70. The pulling action on plate 45 therefore translates into the action of first segment 16 pivoting about primary pivot point 9 as the first segment 16 is pulled by plate 45.

From the preceding paragraph it should become apparent that because each segment has a primary pivot point along the top edge 26, and that each segment is coupled to the lever arm, that pulling on the lever arm plate 45 causes all segments of the articulated finger assembly 10 to move toward the offset lever arm in a coordinated manner relative to all other segments. This coordinated movement is manifested by each segment bending to a degree equal to that of adjacent segments, and in a preferred embodiment, toward the offset lever arm.

There are several advantages of this stacked plate articulated finger assembly 10 over prior art assemblies. For example, being able to construct the assembly 10 from layers of plates, the inner recesses of the assembly can be reached to build a lever arm within the assembly, and finely tune edges of the plates to slip past each other or pivot precisely where needed. This access to the interior of the assembly is not possible with a solid piece of material.

Another advantage of the stacked plate assembly is that the plates are relatively easy to put together from preformed parts using inexpensive aluminum rivets. Therefore, the entire assembly 10 is economical to assemble.

A related issue is that the assembly is also economical to manufacture. Specifically, the plates are machined from a stack of materials using Wire Electro Discharge Machining (EDM). Using this machining technique, approximately 10 finger assemblies worth of plates can be cut at a single time.

In a preferred assembly process, assembly begins with the most distal segment from the base segment first, working back to the most proximal segment to the base segment. Each successive layer of the next most distal segment overlaps the previous layer, covering up pivot points with pins inserted therein.

An alternative assembly method from the preferred method above would be to construct the assembly beginning from the most outer side, the most proximal segment to the base. Each successive layer is built toward the distal end, and then back to the proximal end of the assembly.

Another feature of the articulated finger assembly that might not be obvious from the description given is that no special restraints are required to keep the pivot pins in place within the assembly. Successive overlapping segments secured by pins through securing holes within overlapping plates force the pivot pins to remain within the pivot holes.

The articulated finger assembly is also a compact design. This is a result of the lever arm being a series of thin and coupled plates. The lever arm mechanism is therefore a relatively small portion of the total assembly.

Another advantage of the assembly is the natural consequence of using segments which overlap or are overlapped by adjacent segments. Overlapping does not create gaps between adjacent segments, where material or other objects could become entangled within the assembly, resulting in damage to parts or loss of articulation.

Figure 5:
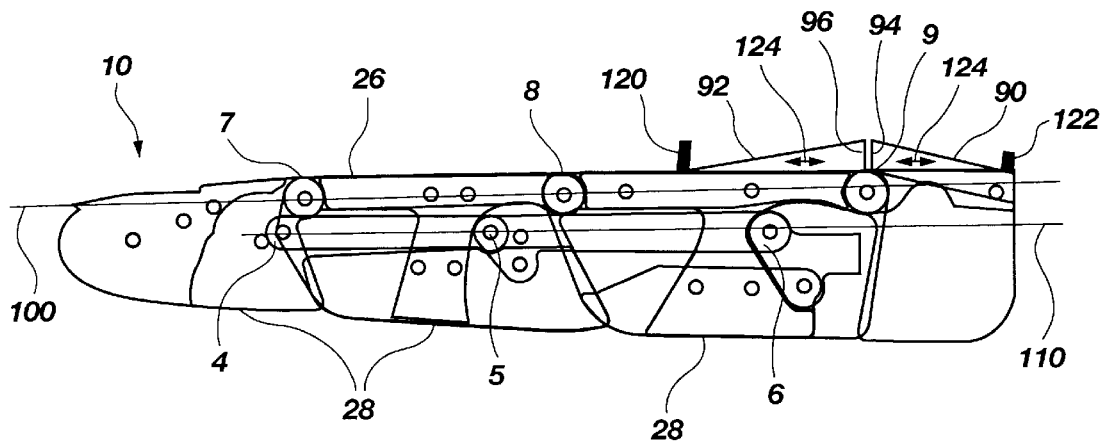
FIG. 5 is an elevational profile view of the artificial finger of FIG. 1, with a range of motion restrictor (stop) coupled to an edge of the finger.

FIG. 5 provides an elevational profile view of the artificial finger of FIG. 1, with an additional feature. Notice that there are now two slanted projections 90 and 92 which extend away from the top edge 26. The projections 90 and 92 slope upward to meet each other at opposing edges 94 and 96. The opposing edges 94 and 96 meet to thereby stop movement of the finger beyond a desired range of motion. Essentially, the finger is prevented from bending backwards.

The projections 90 and 92 essentially fulfill a three-fold purpose. Most importantly, they prevent damage to the finger. Just as a human finger might break when bent beyond its intended and natural range of motion, the artificial finger can also be damaged. Accordingly, the projections 90 and 92 prevent the artificial finger from "hyper-extending."

A second possible purpose fulfilled by the projections 90 and 92 is directed to the aspect of simply not wanting the finger to be able to move beyond a selected maximum extension of the finger. In other words, it can be desirable for the finger to always have a maximum range of motion which is certain to a user. This can allow the finger to be used where precision movement is important.

A third possible purpose fulfilled by the projections 90 and 92 is directed to an embodiment of the artificial finger which might not have a single direction of bending motion. In other words, suppose an artificial finger is constructed which can bend in either direction (toward a palm or away from the palm). The projections 90 and 92 ensure that bending motion is in only one particular direction. Accordingly, it is envisioned that in such a multi-directional finger, the projections 90 and 92 might be relocatable on an opposite edge of the finger, enabling movement in a direction opposite to a first bending direction.

It should also be apparent that the projections 90 and 92 might be relocatable even on a same top edge 26. This means that the projections 90 and 92 might be constructed so as to slide away from or toward each other along the top edge 26. In this way, the range of motion (bending) of the finger might be adjustable, allowing for some degree of hyper-extension of the finger.

Figure 6:
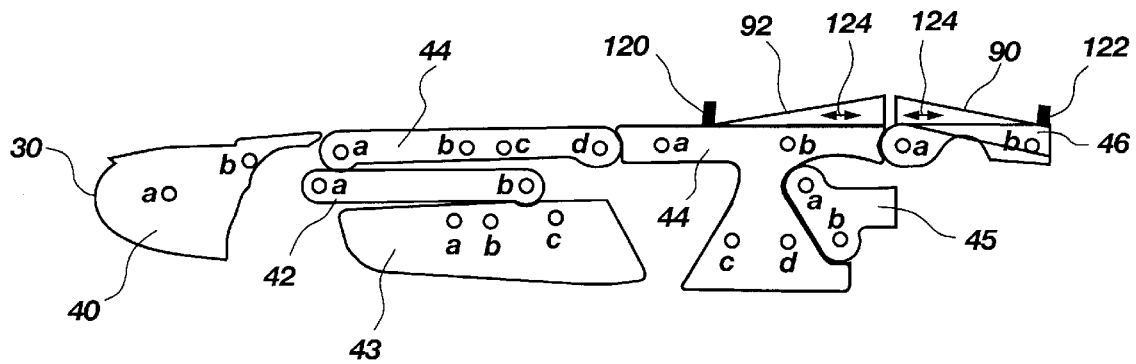
FIG. 6 is an elevational profile view of the artificial finger of FIG. 3A, showing that the range of motion restrictor of FIG. 5 is coupled to the center finger plates.

FIG. 6 is provided to show an elevational view of the artificial finger of FIG. 3A, showing that the range of motion restrictor of FIG. 5 is coupled to two of the center finger plates 44 and 46.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. The projections 90 and 92 are made slidable, for example, by being disposed within a groove along the top edge of plate 44 (see FIG. 6). The projections 90 and 92 can be secured to plate 44 by any means known to those skilled in the art. For example, movable barriers 120 and 122 are attached to each of the projections 90 and 92. By securing the movable barriers 120 and 122 to the plate 44, sliding movement by the projections 90 and 92 is stopped. Arrows 124 indicate the directions in which the projections 90 and 92 are capable of sliding.

What is claimed is:

1. An artificial finger assembly which provides a range of motion of a human finger, said artificial finger assembly comprising:
   a plurality of finger segments, each finger segment formed of a plurality of stacked and aligned plates, and being coupled to an adjacent finger segment at a common pivot point;
   a lever arm means for actuating the plurality of finger segments, and being associated with the plurality of finger segments so as to cause each finger segment to pivot around an associated common pivot point;
   a first projection coupled on an outer edge of a plate of a last finger segment that is closest to a hand assembly, wherein the first projection is coupled to the outer edge of the last finger segment so as to be slidably engaged, thereby enabling the maximum extension of the artificial finger assembly to be adjustable according to a location of where the first projection is secured to the last finger segment; and
   a second projection coupled on an outer edge of a plate of a next to last finger segment which is disposed so as to be in pivoting engagement with the last finger segment, wherein the first projection is abutted against the second projection when the artificial finger assembly is extended to a maximum extension.

2. The artificial finger assembly as defined in claim 1 wherein the common pivot point of each of the plurality of finger segments is disposed near but not on an edge of an end thereof such that the adjacent finger segments overlap.

3. The artificial finger assembly as defined in claim 2 wherein said artificial finger assembly further comprises:
   a first finger segment including at least two most distal finger plates;
   a second finger segment including at least three next most distal finger plates, wherein the at least two most distal finger plates are interleaved between the at least three next most distal finger plates and coupled therebetween at a first common pivot point;
   a third finger segment including at least four next most distal finger plates, wherein the at least three next most distal finger plates are interleaved between the at least four next most distal finger plates and coupled therebetween at a second common pivot point; and
   a fourth finger segment including at least five next most distal finger plates, wherein the at least four next most distal finger plates are interleaved between the at least five next most distal finger plates and coupled therebetween at a third common pivot point, and wherein the fourth finger segment can be coupled to a hand assembly.

4. The artificial finger assembly as defined in claim 1 wherein the lever arm means comprises an articulated lever arm having a plurality of lever arm segments, each lever arm segment being associated with a finger segment for actuating said associated finger segment.

5. The artificial finger assembly as defined in claim 4 wherein the common pivot point of each finger segment is located along a top edge of the artificial finger assembly.

6. The artificial finger assembly as defined in claim 5 wherein the articulated lever arm is offset from the common pivot point of each finger segment so as to cause each finger segment to bend toward the articulated lever arm.

7. The artificial finger assembly as defined in claim 6 wherein the articulated lever arm is disposed in the interior of the artificial finger assembly.

8. The artificial finger assembly as defined in claim 4 wherein the assembly comprises at least two finger segments and at least two associated lever arm segments.

9. The artificial finger assembly as defined in claim 4 wherein each lever arm segment and associated finger segment is coupled at a second pivot point to an adjacent lever arm segment and associated finger segment.

10. The artificial finger assembly as defined in claim 9 wherein each common pivot point and each second pivot point comprises a hole with a pin inserted therethrough.

11. The artificial finger assembly as defined in claim 10 wherein the pins inserted through the common pivot point are selected from the group of materials consisting of aluminum and stainless steel.

12. The artificial finger assembly as defined in claim 1 wherein the second projection is coupled to the outer edge of the next to last finger segment so as to be slidably engaged, thereby enabling the maximum extension of the artificial finger assembly to be adjustable according to a location of where the second projection is secured to the next to last finger segment.

13. An artificial body segment assembly which provides a range of motion of a body segment, said artificial body segment assembly comprising:
   a plurality of body segments, each body segment formed of a plurality of stacked and aligned plates, and being coupled to an adjacent body segment at a common pivot point; and
   a lever arm means for actuating the plurality of body segments, and being associated with the plurality of body segments so as to cause each body segment to pivot around an associated common pivot point;
   a first projection coupled on an outer edge of a plate of a last body segment that is closest to a hand assembly, wherein the first projection is coupled to the outer edge of the last body segment so as to be slidably engaged, thereby enabling the maximum extension of the artificial body assembly to be adjustable according to a location of where the first projection is secured to the last body segment; and
   a second projection coupled on an outer edge of a plate of a next to last body segment which is disposed so as to be in pivoting engagement with the last body segment, wherein the first projection is abutted against the second projection when the artificial body assembly is extended to a maximum extension.

14. The artificial body segment assembly as defined in claim 13 wherein the common pivot point of each of the plurality of body segments is disposed near but not on an edge of an end thereof such that the adjacent body segments overlap.

15. The artificial body assembly as defined in claim 14 wherein said artificial body assembly further comprises:
   a first body segment including at least two most distal body plates;
   a second body segment including at least three next most distal body plates, wherein the at least two most distal body plates are interleaved between the at least three next most distal body plates and coupled therebetween at a first common pivot point;
   a third body segment including at least four next most distal body plates, wherein the at least three next most distal body plates are interleaved between the at least four next most distal body plates and coupled therebetween at a second common pivot point; and
   a fourth body segment including at least five next most distal body plates, wherein the at least four next most distal body plates are interleaved between the at least five next most distal body plates and coupled therebetween at a third common pivot point, and wherein the fourth body segment can be coupled to a hand assembly.

16. The artificial body segment assembly as defined in claim 13 wherein the lever arm means comprises an articulated lever arm having a plurality of lever arm segments, each lever arm segment being associated with a body segment for actuating said associated body segment.

17. The artificial body segment assembly as defined in claim 16 wherein the assembly comprises at least two body segments and at least two associated lever arm segments.

18. The artificial body segment assembly as defined in claim 16 wherein each lever arm segment and associated body segment is coupled at a second pivot point to an adjacent lever arm segment and associated body segment.

19. The artificial body segment assembly as defined in claim 18 wherein each common pivot point and each second pivot point comprises a hole with a pin inserted therethrough.

20. The artificial body segment assembly as defined in claim 19 wherein the pins inserted through the common pivot point are selected from the group of materials consisting of aluminum and stainless steel.

21. The artificial body segment assembly as defined in claim 16 wherein the common pivot point of each body segment is located along a top edge of the artificial body segment assembly.

22. The artificial body segment assembly as defined in claim 21 wherein the articulated lever arm is offset from the common pivot point of each body segment so as to cause each body segment to bend toward the articulated lever arm.

23. The artificial body segment assembly as defined in claim 22 wherein the articulated lever arm is disposed in the interior of the artificial body segment assembly.

24. The artificial body segment assembly as defined in claim 13 wherein the second projection is coupled to the outer edge of the second stacked and aligned plate so as to be slidably engaged, thereby enabling the maximum extension of the artificial body segment assembly to be adjustable according to a location of where the second projection is secured to the second stacked and aligned plate.

25. A method for creating an artificial finger assembly comprising the steps of:
   1) providing a plurality of finger segments formed of a plurality of stacked and aligned plates;
   2) coupling the stacked and aligned plates to an adjacent finger segment at a common pivot point;
   3) providing a lever arm means for actuating the plurality of finger segments so as to cause each finger segment to pivot around an associated common pivot point;
   4) restricting a range of motion of the artificial finger assembly by providing a barrier to movement thereof, wherein the range of motion is adjustable by providing a movable barrier so as to selectively determine when the movable barrier obstructs motion of the artificial finger assembly.

26. The method for creating an artificial finger assembly as defined in claim 25 wherein providing a plurality of stacked plates to form finger segments comprises:
   1) stacking finger plate material that will form a same type of finger segment; and
   2) machining the finger plate material at a same time by Wire Electro Discharge Machining (EDM).

27. The method for creating an artificial finger assembly as defined in claim 26 wherein the step of providing a lever arm means includes the step of providing a plurality of lever arm plates coupled to the plurality of finger segments at second pivot points such that the second pivot points are offset to one side of the common pivot points so that actuating the lever arm plates causes the finger segments to pivot toward the lever arm plates.

28. The method for creating an artificial finger assembly as defined in claim 26 wherein the step of providing the plurality of stacked and aligned finger segments comprises the steps of:

1) constructing a most distal finger segment by stacking and aligning said plurality of plates; and
2) constructing next most distal finger segments back to a most proximal finger segment.

29. The method for creating an artificial finger assembly as defined in claim 28 wherein said assembly leaves no gaps between adjacent finger segments so as to prevent material or other objects from becoming lodged therebetween.

30. The method for creating an artificial finger assembly as defined in claim 26 wherein the step of providing the plurality of stacked and aligned finger segments comprises the steps of:

1) obtaining a most proximal finger segment;
2) coupling a next most proximal finger segment at a first common pivot point to the most proximal finger segment;
3) adding additional finger segments while interleaving between adjacent finger segments until reaching a most proximal finger segment; and
4) adding additional finger segments while moving back towards the most proximal finger segment until a last finger segment added is a last most proximal finger segment.

31. The method for creating an artificial finger assembly as defined in claim 30 wherein said assembly leaves no gaps between adjacent finger segments so as to prevent material or other objects from becoming lodged therebetween.

32. The method for creating an artificial finger assembly as defined in claim 25 wherein the step of coupling the plurality of stacked plates method includes the step of coupling the finger segments so that more distal finger segments are partially overlapped by immediately adjacent proximal finger segments at common pivot points so as to prevent removal of pivot pins inserted therethrough.

* * * * *